United States Patent
Jaseer et al.

(10) Patent No.: US 12,037,301 B1
(45) Date of Patent: Jul. 16, 2024

(54) CHROMIUM-CATALYZED ETHYLENE OLIGOMERIZATION WITH BULKY FUNCTIONALIZED N-ARYL BISPHOSPHINEAMINE LIGANDS

(71) Applicants: King Fahd University of Petroleum and Minerals, Dhahran (SA); Saudi Arabian Oil Company, Dhahran (SA)

(72) Inventors: Ea Jaseer, Kanuur (IN); Samir Barman, Midnapore West (IN); Nestor Garcia Villalta, Saragossa (ES); Motaz Khawaji, Thuwal (SA); Wei Xu, Thuwal (SA)

(73) Assignees: King Fahd University of Petroleum and Minerals, Thuwal (SA); Saudi Arabian Oil Company, Dhahran (SA)

( * ) Notice: Subject to any disclaimer, the term of this patent is extended or adjusted under 35 U.S.C. 154(b) by 46 days.

(21) Appl. No.: 18/068,695

(22) Filed: Dec. 20, 2022

(51) Int. Cl.
 *C07C 2/36* (2006.01)
 *B01J 31/14* (2006.01)
 *B01J 31/22* (2006.01)

(52) U.S. Cl.
 CPC .............. *C07C 2/36* (2013.01); *B01J 31/143* (2013.01); *B01J 31/22* (2013.01); *C07C 2531/14* (2013.01); *C07C 2531/22* (2013.01)

(58) Field of Classification Search
 CPC ... C07C 2/36; C07C 2531/14; C07C 2531/22; B01J 31/143; B01J 31/22
 USPC ........................................................ 585/513
 See application file for complete search history.

(56) References Cited

U.S. PATENT DOCUMENTS

| | | |
|---|---|---|
| 7,273,959 B2 | 9/2007 | Drent et al. |
| 7,297,832 B2 | 11/2007 | Blann et al. |
| 7,300,904 B2 | 11/2007 | Dixon et al. |
| 7,964,763 B2 | 6/2011 | Dixon et al. |
| 8,637,721 B2 | 1/2014 | Fritz et al. |
| 8,864,978 B2 | 10/2014 | Choi |
| 9,035,119 B2 | 5/2015 | Ewart et al. |
| 9,487,456 B2 | 11/2016 | Overett et al. |
| 11,260,381 B2 | 3/2022 | Klosin et al. |
| 11,484,871 B1 | 11/2022 | Jaseer et al. |
| 11,529,622 B2 | 12/2022 | Jaseer et al. |
| 2011/0086991 A1* | 4/2011 | Dixon ........................ C07C 2/32 526/139 |

OTHER PUBLICATIONS

Notification of Transmittal of the International Search Report and the Written Opinion of the International Searching Authority, or the Declaration dated Feb. 9, 2024 pertaining to International application No. PCT/US2003/031990 filed Sep. 5, 2023, pp. 1-12.

Killian el al: "The use of bis(diphenylphosphino)amines with N-aryl functionalities in selective ethylene tri- and tetramerisation", May 7, 2007, pp. 214-218, vol. 270, No. 1-2, Journal of Molecular Catalysis A: Chemical, Elsevier, Amsterdam, NL.

\* cited by examiner

*Primary Examiner* — Prem C Singh
*Assistant Examiner* — Francis C Campanell
(74) *Attorney, Agent, or Firm* — DINSMORE & SHOHL LLP

(57) ABSTRACT

A catalyst system is disclosed. The catalyst system may include a pre-catalyst and a co-catalyst. The pre-catalyst includes one or more chromium compounds coordinated with a ligand. The co-catalyst includes one or more organoaluminum compounds, wherein: the ligand has a structure according to formula (I):

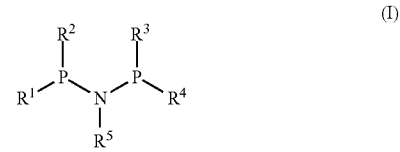

In formula (I), $R^1$, $R^2$, $R^3$, and $R^4$ are independently chosen from ($C_6$-$C_{60}$) aryl, optionally substituted with one or more $R^S$, wherein $R^S$ is a ($C_1$-$C_{50}$) hydrocarbyl or a ($C_1$-$C_{50}$) heterohydrocarbyl. In formula (I), $R^5$ is a ($C_9$-$C_{60}$) aryl or a ($C_4$-$C_{60}$) heteroaryl, optionally substituted with one or more $R^S$, wherein $R^S$ is a ($C_1$-$C_{50}$) hydrocarbyl or a ($C_1$-$C_{50}$) heterohydrocarbyl, provided that $R^5$ is not naphthyl or triptycenyl.

14 Claims, No Drawings

CHROMIUM-CATALYZED ETHYLENE OLIGOMERIZATION WITH BULKY FUNCTIONALIZED N-ARYL BISPHOSPHINEAMINE LIGANDS

TECHNICAL FIELD

Embodiments of the present disclosure generally relate to tetramerization of ethylene and, more particularly, catalyst systems utilized in such chemical processing.

BACKGROUND

Linear alpha-olefins ("LAOs") are typically produced via the cracking of refinery products or the non-selective oligomerization of ethylene, which results in a broad alpha-olefin distribution. Currently, there are several industrial processes that produce LAOs, such as the Shell Higher Olefin Process ("SHOP"), which has been in operation since 1977. SHOP employs a combination of oligomerization and olefin metathesis chemistries to produce a variety of LAOs using a nickel-based catalyst. INEOS, a global manufacturer of petrochemicals, has also developed a proprietary process for synthesizing a wide range of LAOs with the flexibility to change distributions of products to meet demand.

However, demand for LAOs is rising in North America, Western Europe, and Asia. In particular, demand for short chain alpha olefins, such as 1-octene and 1-hexene, is rising due to the significance of these compounds in a number of specific applications. For example, 1-octene may be used to improve the rheological melt and solid resin properties of polyethylene. As a result, the main consumer of 1-octene is the industry responsible for the high-volume production of linear low-density polyethylene ("LLDPE") and high-density polyethylene ("HDPE"), which expands each year. The content of 1-octene may be from 1% to 2% in HDPE, and as much as 10% in some LLDPE grades.

Consequently, there exists significant market demand for 1-octene as a polymer feedstock. Various catalysts have been developed for the tetramerization of ethylene to selectively form 1-octene. However, these catalysts have deficiencies in several respects. For example, the catalysts are not selective and when a catalyst system is used in the reaction of ethylene to form 1-octene, various polymeric side-products may form, resulting in "fouling" of the reactor.

SUMMARY

There is an ongoing need for improved catalysts and/or catalyst systems for the tetramerization of ethylene to selectively produce 1-octene. The catalysts of this disclosure include catalysts comprising a PNP (phosphorous-nitrogen-phosphorous) ligand that may coordinate with one or more chromium compounds to form a catalyst or pre-catalyst. The catalysts may selectively tetramerize 1-ethylene to produce 1-octene, and, thereby, reduce fouling caused by the production of other polymers and other olefins.

Embodiments of the present disclosure include a catalyst system. The catalyst system includes a pre-catalyst comprising one or more chromium compounds that may be coordinated with a ligand, and a co-catalyst comprising one or more organoaluminum compounds. The ligand has a structure according to formula (I):

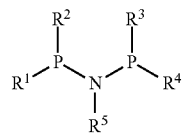

In formula (I), $R^1$, $R^2$, $R^3$, and $R^4$ are independently chosen from $(C_6\text{-}C_{60})$ aryl, optionally substituted with one or more $R^S$, wherein $R^S$ is a $(C_1\text{-}C_{50})$ hydrocarbyl or a $(C_1\text{-}C_{50})$ heterohydrocarbyl; and $R^5$ is a $(C_9\text{-}C_{60})$ aryl or a $(C_4\text{-}C_{60})$ heteroaryl, optionally substituted with one or more $R^S$, wherein $R^S$ is a $(C_1\text{-}C_{50})$ hydrocarbyl or a $(C_1\text{-}C_{50})$ heterohydrocarbyl, provided that $R^5$ is not naphthyl or triptycenyl.

According to one or more embodiments, methods for tetramerizing ethylene to form 1-octene include contacting ethylene with the catalyst system of this disclosure to form a reaction product comprising 1-octene.

DETAILED DESCRIPTION

The present disclosure describes catalyst systems that may be utilized to produce 1-octene from ethylene by tetramerization. Also described are methods for utilizing such catalyst systems. The catalyst systems of this disclosure may include a pre-catalyst and a co-catalyst, which are described in detail. In some embodiments, the pre-catalyst may include one or more chromium compounds and a ligand; and the co-catalyst may include one or more organoaluminum compounds.

In one or more embodiments, the catalyst systems described in the present disclosure may be used to selectively tetramerize ethylene to produce 1-octene, while decreasing the production of polymeric impurities-sometimes referred to as "fouling"-when compared to other known catalysts. Fouling may occur at least partially due to the formation of solid polyethylene-based residues, which may reduce fluid flow and/or fully block or at least partially block fluids in a reactor system from flowing at a reactive rate. Without being bound by any particular theory, it is believed that the incorporation of the ligand described in the present disclosure into the catalyst system reduces fouling while maintaining a suitable yield of 1-octene.

It should be understood that the catalyst systems of this disclosure may be embodied in different forms and should not be construed as limited to the specific embodiments set forth in this disclosure. Rather, embodiments are provided so that this disclosure will be thorough and complete, and will fully convey the scope of the subject matter to those skilled in the art.

Common abbreviations are listed below:

Me: methyl; Et: ethyl; Ph: phenyl; Bn: benzyl; i-Pr: iso-propyl; t-Bu: tert-butyl; THF: tetrahydrofuran; $Et_2O$: diethyl ether; $CH_2Cl_2$: dichloromethane; $CD_2Cl_2$: deuterated dichloromethane; $C_6D_6$: deuterated benzene or benzene-$d_6$; $CDCl_3$: deuterated chloroform; PhCl: chlorobenzene; $PPh_2Cl$: Chlorodiphenylphosphine; $CH_3CN$: acetonitrile; $Na_2SO_4$: sodium sulfate; $MgSO_4$: magnesium sulfate; HCl: hydrogen chloride; $Cr(acac)_3$: chromium (III) acetylacetonate; $N_2$: nitrogen gas; PhMe: toluene; PPR: parallel polymerization reactor; EAO: ethylaluminoxane; MAO: methylaluminoxane; MMAO: modified methylaluminoxane; $Et_3N$: triethylamine; NMR: nuclear magnetic resonance; mmol: millimoles; μmol: micromoles; mL: milliliters; M: molar; min or mins: minutes; h or hrs: hours; d: days; rpm: revolution per minute; STP: standard pressure and temperature.

The term "catalyst" refers to any substance that increases the rate of a specific chemical reaction. Catalysts described in this disclosure may be utilized to promote various reactions, such as, but not limited to, the tetramerization of ethylene to form 1-octene. It should be understood in the art that the catalytic activity may decrease over time, and, therefore, the catalysts may need to be replaced and/or regenerated.

The term "pre-catalyst" refers to a compound that may be catalytically inactive, and when combined with an activator or co-catalyst may be rendered catalytically active. As used herein, the terms "co-catalyst" and "activator" are interchangeable terms that refer to a compound that chemically reacts with a pre-catalyst in a manner that renders the pre-catalyst catalytically active.

The term "catalyst system" refers to one or more chemical species that is catalytically active, may be rendered catalytically active, or affects the catalytic activity. Catalyst systems may include a pre-catalyst and a co-catalyst. Catalyst systems may include additional components, such as, for example, additional co-catalysts or additives, such as scavengers.

The term "independently chosen" is used herein to indicate that the R groups, such as, $R^1$, $R^2$, $R^3$, and $R^4$ can be identical or different (e.g., $R^1$, $R^2$, $R^3$, and $R^4$ may all be substituted alkyls or $R^1$ and $R^2$ may be a substituted alkyl and $R^3$ may be an aryl, etc.). A chemical name associated with an R group is intended to convey the chemical structure that is recognized in the art as corresponding to that of the chemical name. Thus, chemical names are intended to supplement and illustrate, not preclude, the structural definitions known to those of skill in the art.

The term "organoaluminum compound" refers to any chemical compound that includes at least one aluminum atom and at least one aluminum-carbon bond. It should be appreciated that the co-catalyst may include several organoaluminum compounds, or may be comprised of a single organoaluminum compound.

The term "reaction product" refers to a chemical species formed from the reaction of any one or more reactant species or reagents. A reaction product may result in a covalent or ionic bond, coordination, or other interaction between reactant species. In one or more embodiments, one or more reaction products may result from the reaction of the reactant species, and all of these possible produced chemical species are included in the reaction product.

When used to describe certain carbon atom-containing chemical groups, a parenthetical expression having the form "$(C_x\text{-}C_y)$" means that the unsubstituted form of the chemical group has from x carbon atoms to y carbon atoms, inclusive of x and y. For example, a $(C_1\text{-}C_{50})$ alkyl is an alkyl group having from 1 to 50 carbon atoms in its unsubstituted form. In some embodiments and general structures, certain chemical groups may be substituted by one or more substituents, $R^S$. An $R^S$-substituted chemical group defined using the "$(C_x\text{-}C_y)$" parenthetical may contain more than y carbon atoms depending on the identity of any groups $R^S$. For example, a "$(C_1\text{-}C_{50})$ alkyl substituted with exactly one group $R^S$, where $R^S$ is phenyl (—$C_6H_5$)" may contain from 7 to 56 carbon atoms. Thus, in general when a chemical group defined using the "$(C_x\text{-}C_y)$" parenthetical is substituted by one or more carbon atom-containing substituents $R^S$, the minimum and maximum total number of carbon atoms of the chemical group is determined by adding to both x and y the combined sum of the number of carbon atoms from all of the carbon atom-containing substituents $R^S$.

The term "—H" means a hydrogen or hydrogen radical that is covalently bonded to another atom. "Hydrogen" and "—H" are interchangeable, and unless clearly specified have identical meanings. The term "heteroatom," refers to an atom other than hydrogen or carbon.

The term "substitution" means that at least one hydrogen atom ("—H") bonded to a carbon atom or heteroatom of a corresponding unsubstituted compound or functional group is replaced by a substituent (e.g., $R^S$). Except where otherwise defined, substituents may be any suitable functional group or radical that could replace a hydrogen atom bonded to a carbon atom or heteroatom of a corresponding unsubstituted compound. For example, substituents may include, but are not limited to, hydrocarbyls, cyclohydrocarbyls, aryls, halogens, and amines.

The term "halogen atom" or "halogen" means the radical of a fluorine atom (F), chlorine atom (Cl), bromine atom (Br), or iodine atom (I). The term "halide" means anionic form of the halogen atom: fluoride ($F^-$), chloride ($Cl^-$), bromide ($Br^-$), or iodide ($I^-$).

The term "saturated" means lacking any carbon-carbon double bonds, carbon-carbon triple bonds, carbon-nitrogen double bonds, carbon-nitrogen triple bonds, or any carbon-oxygen, carbon-phosphorous, and carbon-silicon double bonds. Where a saturated chemical group is substituted by one or more substituents $R^S$, one or more double and/or triple bonds optionally may be present in substituents $R^S$. The term "unsaturated" means containing one or more carbon-carbon double bonds, carbon-carbon triple bonds, carbon-nitrogen double bonds, carbon-nitrogen triple bonds, carbon-oxygen double bonds, carbon-phosphorous double bonds, or carbon-silicon double bonds, not including double or triple bonds that may be present in substituents $R^S$, if any, or in aromatic rings or heteroaromatic rings, if any.

The term "$(C_1\text{-}C_{50})$ hydrocarbyl" means a hydrocarbon radical of from 1 to 50 carbon atoms, in which each hydrocarbon radical is aromatic or non-aromatic, saturated or unsaturated, straight chain or branched chain, cyclic (having three carbons or more, and including mono-, bi-, and polycyclic, fused and non-fused) or acyclic, and substituted by one or more $R^S$ or unsubstituted. In this disclosure, a $(C_1\text{-}C_{50})$ hydrocarbyl may be an unsubstituted or substituted $(C_1\text{-}C_{50})$ alkyl, $(C_3\text{-}C_{20})$ cycloalkyl, $(C_3\text{-}C_{20})$ cycloalkyl-$(C_1\text{-}C_{20})$ alkylene, $(C_6\text{-}C_{40})$ aryl, or $(C_6\text{-}C_{20})$ aryl-$(C_1\text{-}C_{20})$ alkylene (such as benzyl ($C_6H_5$—$CH_2$—)).

The term "$(C_1\text{-}C_{50})$ alkyl" means a saturated straight or branched hydrocarbon radical of from 1 to 50 carbon atoms that is unsubstituted or substituted by one or more $R^S$. Examples of unsubstituted $(C_1\text{-}C_{50})$ alkyl are unsubstituted $(C_1\text{-}C_{20})$ alkyl; unsubstituted $(C_1\text{-}C_{10})$ alkyl; unsubstituted $(C_1\text{-}C_5)$ alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1\text{-}C_{50})$ alkyl are substituted $(C_1\text{-}C_{20})$ alkyl, substituted $(C_1\text{-}C_{10})$ alkyl, and $[C_{50}]$alkyl. The term "$[C_{50}]$ alkyl" means there is a maximum of 50 carbon atoms in the radical, including substituents, and is, for example, a $(C_{27}\text{-}C_{45})$ alkyl substituted by one $R^S$, which is a $(C_1\text{-}C_5)$ alkyl, respectively. Each $(C_1\text{-}C_5)$ alkyl may be methyl, ethyl, 1-propyl, 1-methylethyl, or 1,1-dimethylethyl.

The term "cyclohydrocarbyl" means an aromatic or non-aromatic cyclic hydrocarbyl having at least three carbon atoms, including mono-, bi-, and polycyclic hydrocarbyls, fused and non-fused; saturated or unsaturated cyclic hydrocarbyls; and substituted or unsubstituted cyclic hydrocarbyls.

The term "$(C_3-C_{20})$ cycloalkyl" means a saturated cyclic hydrocarbon radical of from 3 to 20 carbon atoms that is unsubstituted or substituted by one or more $R^S$. Examples of unsubstituted $(C_3-C_{20})$ cycloalkyl are unsubstituted $(C_3-C_{10})$ cycloalkyl, cyclopropyl, cyclobutyl, cyclopentyl, cyclohexyl, cycloheptyl, cyclooctyl, cyclononyl, and cyclodecyl.

The term "heterohydrocarbyl" refers to a hydrocarbyl, from which at least one carbon atom has been replaced with a heteroatom. Examples of heteroatoms include, without limitation, oxygen, nitrogen, sulfur, and phosphorus. The term "$(C_1-C_{50})$ heterohydrocarbyl" means a heterohydrocarbon radical of from 1 to 50 carbon atoms. The heterohydrocarbon of the $(C_1-C_{50})$ heterohydrocarbyl has one or more heteroatoms. The radical of the heterohydrocarbyl may be on a carbon atom or a heteroatom. Each $(C_1-C_{50})$ heterohydrocarbyl may be unsubstituted or substituted (by one or more $R^S$), aromatic or non-aromatic, saturated or unsaturated, straight chain or branched chain, cyclic (including mono-, bi-, and polycyclic, fused and non-fused), or acyclic. The term "heteroalkyl" refers to an alkyl from which at least one carbon atom has been replaced with a heteroatom.

The term "$(C_6-C_{60})$ aryl" means an unsubstituted or substituted (by one or more $R^S$) aromatic hydrocarbon radical of from 6 to 60 carbon atoms. The term "aryl" includes monocyclic hydrocarbon aromatic radicals (also called monocyclic aryls), bicyclic hydrocarbon aromatic radicals (also called bicyclic aryls), and polycyclic hydrocarbon aromatic radicals (also called polycyclic aryls). A monocyclic aryl includes one ring that is aromatic; a bicyclic aryl includes two rings, which may be fused or non-fused, and least one of which is aromatic; a polycyclic aryl includes three or more rings, which may be independently fused or non-fused, and at least one of which is aromatic. The radical of the $(C_6-C_{60})$ aryl is present on or in conjugation with one or more aromatic carbon atoms.

Non-limiting examples of unsubstituted $(C_6-C_{60})$ aryls include: unsubstituted $(C_6-C_{50})$ aryl, unsubstituted $(C_8-C_{50})$ aryl, unsubstituted $(C_6-C_{15})$ aryl, unsubstituted $(C_8-C_{18})$ aryl, unsubstituted $(C_6-C_{20})$ aryl, unsubstituted $(C_6-C_{24})$ aryl, phenalenyl; phenanthryl, fluorenyl, tetrahydrofluorenyl, indacenyl, hexahydroindacenyl, indenyl, dihydroindenyl, tetrahydronaphthyl, octahydrophenanthryl, anthracenyl, dihydroanthracenyl, pyrenyl, chrysenyl, triphenylenyl, tetracenyl, perylenyl, corannulenyl, and coronenyl. Non-limiting examples of substituted $(C_6-C_{60})$ aryls include: substituted $(C_6-C_{16})$ aryl, substituted $(C_6-C_{18})$ aryl, substituted $(C_6-C_{20})$ aryl, and substituted $(C_6-C_{24})$ aryl.

Non-limiting examples of $(C_6-C_{60})$ aryls include: phenyl, fluorenyl, tetrahydrofluorenyl, indacenyl, hexahydroindacenyl, indenyl, dihydroindenyl, naphthyl, tetrahydronaphthyl, phenanthryl, octahydrophenanthryl, anthracenyl, dihydroanthracenyl, pyrenyl, chrysenyl, triphenylenyl, phenalenyl, tetracenyl, perylenyl, corannulenyl, coronenyl, and fullerenyl.

The term "$(C_4-C_{60})$ heteroaryl" means an unsubstituted or substituted (by one or more $R^S$) aromatic hydrocarbon radical of from 4 to 60 carbon atoms. The term "heteroaryl" includes monocyclic heteroaromatic hydrocarbon radicals (also called monocyclic heteroaryls), bicyclic heteroaromatic hydrocarbon radicals (also called bicyclic heteroaryls), and polycyclic heteroaromatic hydrocarbon radicals (also called polycyclic heteroaryls). A monocyclic heteroaryl includes one ring that is heteroaromatic; a bicyclic heteroaryl includes two rings, which may be fused or non-fused, and least one of which is heteroaromatic; a polycyclic heteroaryl includes three or more rings, which may be independently fused or non-fused, and at least one of which is heteroaromatic. The radical of the $(C_4-C_{60})$ heteroaryl is present on or in conjugation with one or more aromatic carbon atoms or heteroatoms.

Other heteroaryl groups (e.g., $(C_x-C_y)$ heteroaryl generally, such as $(C_4-C_{12})$ heteroaryl) are defined in an analogous manner as having from x to y carbon atoms (such as 4 to 12 carbon atoms) and being unsubstituted or substituted by one or more than one $R^S$. The monocyclic heteroaryl radical is a 5-membered or 6-membered ring. The 5-membered ring has 5 minus h carbon atoms, wherein h is the number of heteroatoms and may be 1, 2, or 3; and each heteroatom may be O, S, N, or P. Non-limiting examples of 5-membered ring heteroaromatic hydrocarbon radical are pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl. The 6-membered ring has 6 minus h carbon atoms, wherein h is the number of heteroatoms and may be 1 or 2 and the heteroatoms may be N or P. Non-limiting examples of 6-membered ring heteroaromatic hydrocarbon radical are pyridine-2-yl; pyrimidin-2-yl; and pyrazin-2-yl. The bicyclic heteroaromatic hydrocarbon radical can be a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The polycyclic heteroaromatic hydrocarbon radical can be a fused 5,6,5-; 5,6,6-; 6,5,6-; or 6,6,6-ring system. An example of the fused 5,6,5-ring system is 1,7-dihydropyrrolo[3,2-f]indol-1-yl. An example of the fused 5,6,6-ring system is 1H-benzo[f]indol-1-yl. An example of the fused 6,5,6-ring system is 9H-carbazol-9-yl. An example of the fused 6,5,6-ring system is 9H-carbazol-9-yl. An example of the fused 6,6,6-ring system is acrydin-9-yl.

The embodiments of the present disclosure are directed to a catalyst system for tetramerizing ethylene to form 1-octene. In one or more embodiments, the catalyst system includes a pre-catalyst comprising one or more chromium compounds that may be coordinated with a ligand, and co-catalyst comprising one or more organoaluminum compounds.

In embodiments of this disclosure, the pre-catalyst that includes one or more chromium compounds may be comprised of any chromium compound that may be rendered catalytically active for, without limitation, promoting the tetramerization of ethylene to form 1-octene. The one or more chromium compounds may be produced using procedures and methods generally known in the art.

In some embodiments, the one or more chromium compounds includes an organic chromium salt, an inorganic chromium salt, a chromium organometallic complex, or combinations of these. In some embodiments, the one or more chromium compounds includes a chromium trichloride tris-tetrahydrofuran complex, (benzene)tricarbonyl chromium, chromium (III) octanoate, chromium (III) acetylacetonoate, chromium hexacarbonyl, chromium (III) 2-ethylhexanoate, or combinations of these.

In one or more embodiments, the pre-catalyst includes chromium that may be coordinated to a ligand. The ligand may have a structure according to formula (I):

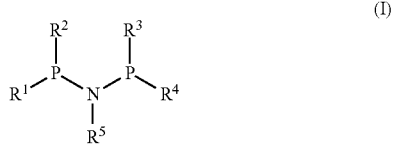
(I)

In formula (I), $R^1$, $R^2$, $R^3$, and $R^4$ are independently chosen from $(C_6-C_{60})$ aryl, optionally substituted with one or more $R^S$, wherein $R^S$ is a $(C_1-C_{50})$ hydrocarbyl or a $(C_1-C_{50})$ heterohydrocarbyl. $R^5$ is a $(C_9-C_{60})$ aryl or a $(C_4-C_{60})$ heteroaryl, provided that $R^5$ is not naphthyl or triptycenyl. $R^5$ may be optionally substituted with one or more $R^S$, wherein $R^S$ is a $(C_1-C_{50})$ hydrocarbyl or a $(C_1-C_{50})$ heterohydrocarbyl, In embodiments, in formula (I), $R^1$, $R^2$, $R^3$, and $R^4$ are independently chosen from unsubstituted $(C_6-C_{16})$ aryl, unsubstituted $(C_6-C_{15})$ aryl, unsubstituted $(C_6-C_{20})$ aryl, and unsubstituted $(C_6-C_{24})$ aryl. In some embodiments, in formula (I), $R^1$, $R^2$, $R^3$, and $R^4$ are independently chosen from a substituted $(C_6-C_{16})$ aryl, a substituted $(C_6-C_{18})$ aryl, a substituted $(C_6-C_{20})$ aryl, and a substituted $(C_6-C_{24})$ aryl.

In various embodiments, when $R^1$, $R^2$, $R^3$, and $R^4$ are independently chosen from $(C_6-C_{60})$ aryl and substituted with one or more $R^S$, $R^S$ is selected from the group consisting of $(C_1-C_{50})$ alkyl or $(C_1-C_{50})$ heteroalkyl. In some embodiments, $R^S$ is selected from the group consisting of methyl, ethyl, 1-propyl, 2-propyl, 1-butyl, 2-butyl, 2-methylpropyl, 1,1-dimethylethyl, 1-pentyl, 1-hexyl, 1-heptyl, 1-nonyl, and 1-decyl.

In some embodiments, in formula (I), $R^1$, $R^2$, $R^3$, and $R^4$ are independently chosen from phenyl, fluorenyl, tetrahydrofluorenyl, indacenyl, hexahydroindacenyl, indenyl, dihydroindenyl, naphthyl, tetrahydronaphthyl, phenanthryl, octahydrophenanthryl, anthracenyl, dihydroanthracenyl, pyrenyl, chrysenyl, triphenylenyl, phenalenyl, tetracenyl, perylenyl, corannulenyl, and coronenyl.

In embodiments, in formula (I), $R^5$ is chosen from an optionally substituted $(C_9-C_{60})$ aryl, an optionally substituted $(C_{12}-C_{60})$ aryl, an optionally substituted $(C_{14}-C_{60})$ aryl, an optionally substituted $(C_{16}-C_{60})$ aryl, an optionally substituted $(C_{18}-C_{60})$ aryl, an optionally substituted $(C_{20}-C_{60})$ aryl, an optionally substituted $(C_{22}-C_{60})$ aryl, and an optionally substituted $(C_{24}-C_{60})$ aryl.

In embodiments, in formula (I), $R^5$ is chosen from an optionally substituted $(C_4-C_{60})$ heteroaryl, an optionally substituted $(C_5-C_{60})$ heteroaryl, an optionally substituted $(C_8-C_{60})$ heteroaryl, an optionally substituted $(C_9-C_{60})$ heteroaryl, an optionally substituted $(C_1-C_{60})$ heteroaryl, in which the heteroatom of the heteroaryl is nitrogen, oxygen or sulfur. In one or more embodiments, $C_4-C_{60}$) heteroaryl, $C_5-C_{60}$) heteroaryl, $(C_8-C_{60})$ heteroaryl, $(C_9-C_{60})$ heteroaryl, or $(C_1-C_{60})$ heteroaryl are substituted with one or more $R^S$, where $R^S$ is $(C_1-C_{20})$alkyl. In one or more embodiments, in formula (I), $R^5$ is chosen from phenalenyl, phenanthryl, fluorenyl, tetrahydrofluorenyl, indacenyl, hexahydroindacenyl, octahydrophenanthryl, anthracenyl, dihydroanthracenyl, pyrenyl, chrysenyl, triphenylenyl, tetracenyl, perylenyl, corannulenyl, coronenyl, and fullerenyl.

In one or more embodiments, in formula (I), $R^5$ is chosen from the radical having formula (II), formula (III), formula (IV), formula (V), formula (VI), or formula (VII), optionally substituted with one or more $R^S$.

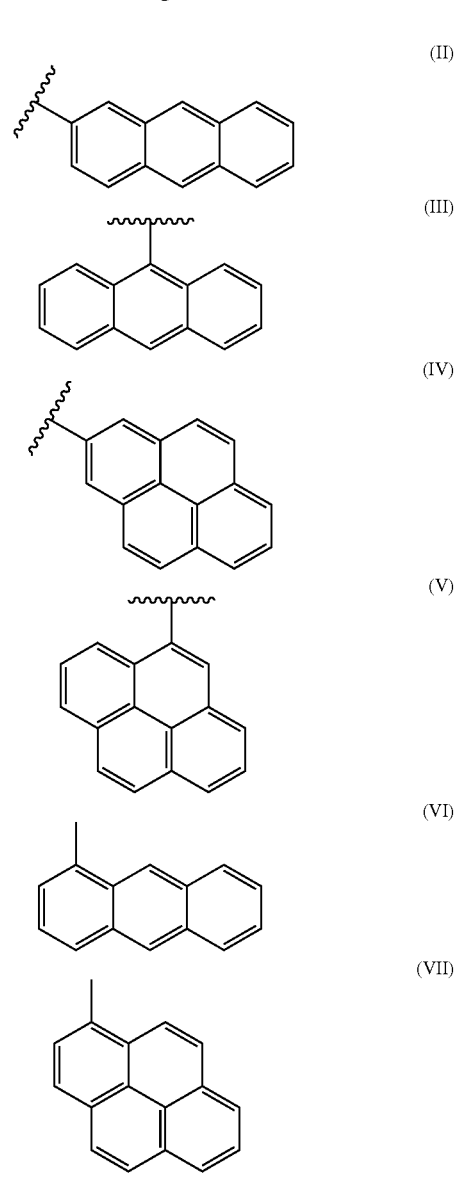

In various embodiments, when $R^5$ is a radical having formula (II), formula (III), formula (IV), formula (V), formula (VI), or formula (VII) substituted with one or more $R^S$, $R^S$ is selected from the group consisting of $(C_1-C_{50})$ alkyl or $(C_1-C_{50})$ heteroalkyl. In some embodiments, $R^S$ is selected from the group consisting of methyl, ethyl, 1-propyl, 2-propyl, 1-butyl, 2-butyl, 2-methylpropyl, 1,1-dimethylethyl, 1-pentyl, 1-hexyl, 1-heptyl, 1-nonyl, and 1-decyl.

In some embodiments when $R^5$ is a radical having formula (II), formula (III), formula (IV), formula (V), formula (VI), or formula (VII), $R^1$, $R^2$, $R^3$, and $R^4$ are each an independently chosen $(C_6-C_{60})$ aryl. In some embodiments, when $R^5$ is a radical having formula (II), formula (III), formula (IV), formula (V), formula (VI), or formula (VII), $R^1$, $R^2$, $R^3$, and $R^4$ are each independently chosen from an unsubstituted $(C_6-C_{15})$ aryl; an unsubstituted $(C_6-C_{20})$ aryl; and an unsubstituted $(C_6-C_{24})$ aryl. In some embodiments when $R^5$ is a radical having formula (II), formula (III), formula (IV), formula (V), formula (VI), or formula (VII), $R^1$, $R^2$, $R^3$, and $R^4$ are each independently chosen from a substituted $(C_6-C_{15})$ aryl; a substituted $(C_6-C_{20})$ aryl; and a substituted (C$_6$-C$_{24}$) aryl. In some embodiments, when R$^5$ is a radical having formula (II), formula (III), formula (IV), formula (V), formula (VI), or formula (VII), R$^1$, R$^2$, R$^3$, and R$^4$ are each independently chosen from phenyl, fluorenyl, tetrahydrofluorenyl, indacenyl, hexahydroindacenyl, indenyl, dihydroindenyl, naphthyl, tetrahydronaphthyl, phenanthryl, octahydrophenanthryl, anthracenyl, dihydroanthracenyl, pyrenyl, chrysenyl, triphenylenyl, phenalenyl, tetracenyl, perylenyl, corannulenyl, coronenyl, and fullerenyl.

The catalyst system may include a pre-catalyst comprising chromium that may be coordinated to a ligand according to formula (I). The pre-catalyst may be catalytically inactive but may be rendered catalytically active by any technique known in the art for activating pre-catalysts of olefin polymerization reactions. For example, the pre-catalyst comprising chromium coordinated to a ligand of formula (I) may be rendered catalytically active by contacting the pre-catalyst to, or combining the pre-catalyst with, a co-catalyst. In the catalytically inactive form chromium may be neutral and in the catalytically active form the chromium may be positively charged due to the loss of one or more monoanionic ligands.

Suitable activating co-catalysts for use herein include alkyl aluminums and polymeric or oligomeric alumoxanes (also known as aluminoxanes). The term "alkyl aluminum" means a monoalkyl aluminum dihydride or monoalkylaluminum dihalide, a dialkyl aluminum hydride or dialkyl aluminum halide, or a trialkylaluminum. Examples of polymeric or oligomeric aluminoxanes include methylaluminoxane, triisobutylaluminum-modified methylaluminoxane, and isobutylaluminoxane.

In some embodiments, the co-catalyst may include at least one organoaluminum compound. In some embodiments, the co-catalyst may include at least one alkyl aluminum compound. The at least one aluminum alkyl compound may, for example, have a structure according to formula (VI):

(VI)

In formula (VI), R$^A$, R$^B$ and R$^C$ are each independently chosen from hydride, hydrogen, an unsubstituted (C$_1$-C$_{20}$) linear or branched alkyl, an oxygen-containing heteroalkyl, or a halogen.

In some embodiments, the at least one aluminum alkyl compound may include trimethylaluminum, triethylaluminum, tripropylaluminum, tri-iso-butylaluminum, diisobutylaluminum hydride, trihexylaluminum, tri-n-octylaluminum, methylaluminum dichloride, ethylaluminum dichloride, dimethylaluminum chloride, diethylaluminum chloride, ethylaluminum sesquichloride, or methylaluminum sesquichloride.

In some embodiments, the at least one alkyl aluminum compound may be an aluminoxane (a partial hydrolysate of a trialkylaluminum compound). Specific embodiments of aluminoxane include, but are not limited to, methylaluminoxane ("MAO"), ethylaluminoxane ("EAO"), aluminum isopropoxide, and modified alkylaluminoxanes, such as modified methylaluminoxane ("MMAO"). As described in the present disclosure, the term "modified alkylaluminoxane" refers to an alkylaluminoxane that includes one or more modifier groups, such as isobuytyl or n-octyl groups in addition to the alkyl groups.

One or more embodiments of this disclosure includes methods of tetramerizing ethylene. In one or more embodiments, the method includes contacting ethylene with the catalyst system to from a reaction product including 1-octene. The phrase "contacting ethylene with the catalyst system" generally may include any mixing and/or combining of the reactant ethylene with the catalyst system. In some embodiments, the catalyst and co-catalyst may be prepared as separate solutions, and then combined, prior to contacting of the catalyst system with ethylene. In some embodiments, the catalyst system may be contacted with ethylene in the presence of one or more reaction mediums. Suitable reaction mediums may include, for example, cyclohexane ("CyH"), methylcyclohexane ("MeCy"), decahydronapthalene ("DHN"), 2,2,4-trimethylpentane ("TMP"), and chlorobenzene ("PhCl"). In some embodiments, the ethylene may be contacted with the catalyst system in the presence of hydrogen.

Any conventional polymerization processes may be employed to tetramerize ethylene. Such conventional polymerization processes include, but are not limited to, solution polymerization processes, slurry phase polymerization processes, and combinations thereof using one or more conventional reactors such as loop reactors, isothermal reactors, stirred tank reactors, batch reactors in parallel, series, or any combinations thereof, for example.

In one or more embodiments, the reaction may be performed as a batch reaction or as a continuous process reaction, such as a continuous stir tank reactor process.

In some embodiments, the pressure of the reactor may be from 2 bar to 100 bar. In various embodiments, the pressure of the reactor may be from 2 bars to 90 bars, 2 bar to 80 bars, 2 bar to 70 bars, 2 bar to 60 bars, 2 bar to 50 bars, 2 bar to 40 bars, 10 bars to 90 bars, 10 bar to 80 bars, 10 bar to 70 bars, 10 bar to 60 bars, 10 bar to 50 bars, 10 bar to 40 bars, 20 bars to 90 bars, 20 bar to 80 bars, 20 bar to 70 bars, 20 bar to 60 bars, 20 bar to 50 bars, 30 bar to 40 bars, 30 bars to 90 bars, 30 bar to 80 bars, 30 bar to 70 bars, 30 bar to 60 bars, 30 bar to 50 bars, 30 bar to 40 bars, 40 bars to 90 bars, 40 bar to 80 bars, 40 bar to 70 bars, 40 bar to 60 bars, 40 bar to 50 bars, 50 bars to 90 bars, 50 bar to 80 bars, 50 bar to 70 bars, or 50 bar to 60 bars. However, reactor pressure outside of these ranges are contemplated, especially in view of the specific design of the reactor system and concentrations of the reactants and catalyst system.

In various embodiments, the reactor temperature may be from 30° C. to 180° C. In one or more embodiments, the reactor temperature may be from 30° C. to 180° C., 30° C. to 170° C., 30° C. to 160° C., 30° C. to 150° C., 30° C. to 140° C., 30° C. to 130° C., 30° C. to 120° C., 30° C. to 110° C., 30° C. to 100° C., 40° C. to 180° C., 40° C. to 170° C., 40° C. to 160° C., 40° C. to 150° C., 40° C. to 140° C., 40° C. to 130° C., 40° C. to 120° C., 40° C. to 110° C., 40° C. to 100° C., 50° C. to 180° C., 50° C. to 170° C., 50° C. to 160° C., 50° C. to 150° C., 50° C. to 140° C., 50° C. to 130° C., 50° C. to 120° C., 50° C. to 110° C., or 50° C. to 100° C. However, process conditions outside of these ranges are contemplated, especially in view of the specific design of the reactor system and concentrations of the reactants and catalyst system.

It should be understood that, in one or more embodiments, similar catalyst systems that do not include the ligand of the present application may exhibit increased fouling compared to the catalyst system of the present application. In one or more embodiments, the inclusion of the ligand in a catalyst system may suppress polymer formation while not greatly reducing the yield of 1-octene. In one or more embodiments, polymer formation (fouling) may be reduced by at least 5%, 10%, 20%, 30%, 40%, 50%, 60%, 70%, 80%, 90%, or even 95% by the inclusion of the ligand. For example, the reaction product of the tetramerization of ethylene using the catalyst system may include less than 15 wt. %, less than 12 wt. %, less than 9 wt. %, less than 6 wt. %, or less than 3 wt. % of polymer.

In one or more embodiments, 1-octene production may be increased, stay the same, or may decrease by less than or equal to 50%, 40%, 30%, 20%, 10% or even 5% by the inclusion of the ligand. For example, the reaction product of the tetramerization of ethylene using the catalyst system may include greater than 50 wt. %, greater than 55 wt. %, greater than 60 wt. %, greater than 65 wt. %, or greater than 70 wt. % of 1-octene.

In one or more embodiments, the catalyst system may both reduce the polymer formation (such as by at least 5%, 10%, 20%, 30%, 40%, 50%, 60%, 70%, 80%. 90% or even 95%) and increase, not effect, or decrease 1-octene production rate by less than or equal to 50%, 40%, 30%, 20%, 10% or even 5%. Reduction in polymer formation rates and catalytic activity on a percentage basis are based on catalyst systems that include the ligand of the present disclosure as compared with catalyst systems that do not include the ligand of the present disclosure.

In one or more embodiments, the catalyst system may have increased activity compared to similar catalyst systems that do not include the ligand of the present disclosure. As used in the present disclosure, the term "activity" refers to the amount of reaction product produced (in kilograms) per the amount of chromium compound used (in grams) per hour ($kg \cdot g_{Cr}^{-1} \cdot h^{-1}$). In some embodiments, the catalyst system may have an activity greater than 10 $kg \cdot g_{Cr}^{-1} \cdot h^{-1}$, greater than 100 $kg \cdot g_{Cr}^{-1} \cdot h^{-1}$, greater than 250 $kg \cdot g_{Cr}^{-1} \cdot h^{-1}$, greater than 500 $kg \cdot g_{Cr}^{-1} \cdot h^{-1}$, greater than 750 $kg \cdot g_{Cr}^{-1} \cdot h^{-1}$, greater than 1,000 $kg \cdot g_{Cr}^{-1} \cdot h^{-1}$, greater than 10,000 $kg \cdot g_{Cr}^{-1} \cdot h^{-1}$.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Additionally, the term "consisting essentially of" is used in this disclosure to refer to quantitative values that do not materially affect the basic and novel characteristic(s) of the disclosure.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

EXAMPLES

The various aspects of the present disclosure will be further clarified by the following examples. The examples are illustrative in nature and should not be understood to limit the subject matter of the present disclosure.

A. Preparation of an N-Aryl PNP Ligands

An N-anthracenyl PNP ligand was formed as depicted in Reaction Scheme 1:

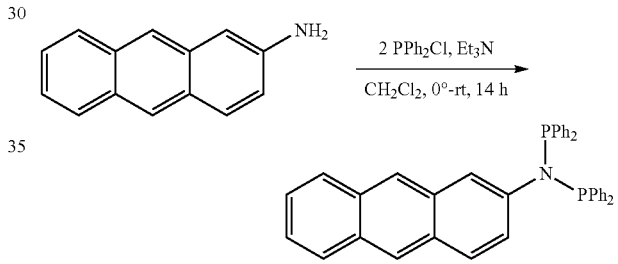

To a solution of 2-aminoanthracene (1.55 mmol) and triethylamine (4.34 mmol) in 5 mL dichloromethane, Ph$_2$PCl (3.1 mmol) was slowly added at 0° C. The mixture was stirred for 1 hour then allowed to warm up to room temperature and stirring continued for an additional 14 hours. The volatiles were removed under reduced pressure and the residue was extracted with anhydrous THF (3×2 mL). The THF was then removed and the remaining solid residue was triturated with anhydrous CH$_3$CN (5×3 mL) followed by vacuum drying at 65° C. to give ligand in 59% yield. $^1$H NMR (CD$_2$Cl$_2$): 6.9-8.4 ppm (Ar-pH); $^{31}$P NMR: 66.27 ppm.

An N-pyrenyl PNP ligand was formed as depicted in Reaction Scheme 2:

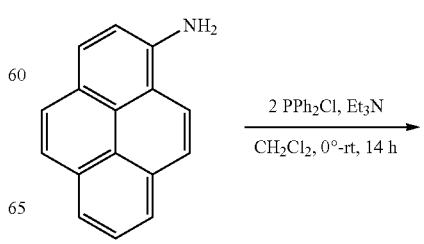

-continued

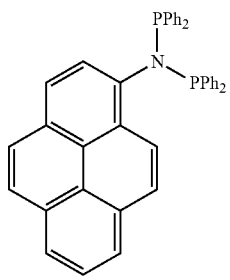

To a solution of 1-aminopyrene (1.55 mmol) and triethylamine (4.34 mmol) in 5 mL dichloromethane, $Ph_2PCl$ (3.1 mmol) was slowly added at 0° C. The mixture was stirred for 1 h then allowed to warm up to room temperature and stirring continued for an additional 14 h. The volatiles were removed under reduced pressure and the residue was extracted with anhydrous THF (3×2 mL). The THF was then removed and the remaining solid residue was triturated with anhydrous $CH_3CN$ (5×3 mL) followed by vacuum drying at 65° C. to give ligand in 65% yield. $^1H$ NMR ($CD_2Cl_2$): 7.18-8.25 ppm (Ar-pH); $^{31}P$ NMR: 62.67 ppm.

B. Ethylene Tetramerization

The catalytic reactions were performed in a magnetically stirred (1000 rpm) 250 mL stainless steel (vessel) Buchi reactor system. The reactor was equipped with a propeller-like stirrer and injection barrel for charging the solvent and the reagents. The reactor was heated to 110° C., purged several times with argon gas and ethylene to remove air and moisture, and then cooled. Aluminoxane was measured in the glovebox and diluted with a solvent, in this case chlorobenzene, to a total volume of 95 mL. $Cr(acac)_3$ and ligands were dissolved with the corresponding solvent (1 mL each) in a separate vial, mixed together and diluted to 5 mL. When the reaction medium was cyclohexane, Cr complex was dissolved in chlorobenzene. Co-catalyst solution, followed by pre-catalyst solution, were transferred to the reactor and pressurized with ethylene at 45 bar. The reaction temperature was maintained constant during the reaction by circulating hot oil in the jacket and by allowing the cool liquid to flow from the chiller through the cooling coil present inside the reactor vessel.

At the end of the stipulated time, 1.0 mL methanol was added to quench the reaction. The reactor vessel was cooled to approximately 15° C. and then depressurized very slowly using a needle valve. After depressurizing, an aliquot of this liquid mixture was quantified by gas chromatographic analysis. The remaining whole reaction mixture containing the α-olefins/polymer was then added to 50 mL of acidic methanol (5% HCl) and was stirred for 2 hours at room temperature. Then the polymer was filtered and washed with distilled water and stirred for 1 hour with 200 mL water. This process was repeated four times. Then the polymer was filtered and dried overnight in a vacuum oven at 60° C.

The conditions and results of each run are reported in Table 1.

TABLE 1

Example Reaction Conditions and Results

| Entry | $R^5$ | T (° C.) | Solvent | $C_6$ (wt %) | 1-$C_6$ in $C_6$ (%) | $C_8$ (wt %) | 1-$C_8$ in $C_8$ (%) | 1-$C_6$ + 1-$C_8$ (wt %) | $C_{10}$+ (wt %) | PE (wt %) | Activity (kg · $g_{Cr}^{-1}$ · $h^{-1}$) |
|---|---|---|---|---|---|---|---|---|---|---|---|
| E1 | Pyrene | 45 | PhCl | 29.7 | 70.5 | 68.7 | 97.8 | 88.1 | 1.3 | 0.3 | 1774 |
| E2 | Pyrene | 60 | PhCl | 38.1 | 79.1 | 59.9 | 97 | 88.2 | 0.4 | 1.5 | 1206 |
| E3 | Anthracene | 45 | PhCl | 24.2 | 57.3 | 72.1 | 95.6 | 82.8 | 2 | 1.7 | 1479 |
| E4 | Anthracene | 60 | PhCl | 27.9 | 75.7 | 69 | 91 | 83.9 | 0.5 | 2.6 | 687 |
| E5 | Pyrene | 45 | MeCy | 26.3 | 58.9 | 70.7 | 91.9 | 80.5 | 1.8 | 1.2 | 511 |
| E6 | Pyrene | 45 | Cy | 25.1 | 64.5 | 71.7 | 90.2 | 80.9 | 1.6 | 1.5 | 450 |
| E7 | Anthracene | 45 | MeCy | 23.9 | 61.2 | 71.8 | 88.1 | 77.9 | 1.7 | 2.6 | 290 |
| E8 | Anthracene | 45 | Cy | 21.5 | 57.5 | 74.1 | 91.6 | 80.2 | 2.6 | 1.8 | 435 |

Reaction Conditions: $Cr(acac)_3$ (1 μmol); L/Cr = 1:1; MMAO-3A (2 mmol, 0.88 mL), Al/Cr = 2000; Solvent (Chlorobenzene (PhCl), Cyclohexane (Cy), methylcyclohexane (MeCy); 45 bar; 10 min

TABLE 2

Comparative Example Reaction Conditions and Results

| Entry | $R^5$ | T (° C.) | Solvent | $C_6$ (wt %) | 1-$C_6$ in $C_6$ (%) | $C_8$ (wt %) | 1-$C_8$ in $C_8$ (%) | 1-$C_6$ + 1-$C_8$ (wt %) | $C_{10}$+ (wt %) | PE (wt %) | Activity (kg · $g_{Cr}^{-1}$ · $h^{-1}$) |
|---|---|---|---|---|---|---|---|---|---|---|---|
| C1 | Isopropyl | 45 | PhCl | 22.8 | 81.6 | 72.0 | 97.1 | 88.5 | 1.6 | 3.5 | 1184 |
| C2 | m-Trifluorotoluyl | 45 | PhCl | 24.1 | 56.1 | 72.5 | 95.2 | 82.5 | 2.6 | 0.8 | 1492 |
| C3 | 1-Triptycenyl | 45 | PhCl | 35.2 | 93.3 | 63.2 | 98.0 | 94.9 | 0.3 | 1.0 | 1544 |

Reaction condition: $Cr(acac)_3$ 1 μmol, L/Cr 1:1, MMAO-3A 2 mmol (Al/Cr 2000), PhCl 100 ml, 45 bar, 10 min Table 1 shows the results of tetramerizations using a catalyst system comprising PNP ligands wherein $R^5$ is anthracenyl or pyrenyl. Table 2 provides comparative data: the results of tetramerizations using a chromium (III) acetylacetonoate pre-catalyst comprising either an isopropyl-PNP ligand (a PNP ligand wherein $R^5$ is isopropyl), an m-trifluorotoluyl-PNP ligand (a PNP ligand wherein $R^5$ is an m-CF$_3$—C$_6$H$_4$), or 1-triptycenyl-PNP ligand (a PNP ligand wherein $R^5$ is 1-triptycenyl).

A comparison of the data of Table 1 to that of Table 2 reveals that the reaction using a pre-catalyst with a pyrenyl-PNP ligand resulted in superior overall α-olefin selectivity (E1: 1-C$_6$+1-C$_8$, 88.1 wt %) relative to the analogous reaction employing a pre-catalyst with a less sterically hindered m-trifluorotoluyl-PNP ligand (C2:1-C$_6$+1-C$_8$, 82.5 wt %). Moreover, the system of E1 exhibited notably higher activity (1774 kg·g$_{Cr}^{-1}$·h$^{-1}$) and notably lower polyethylene formation (0.3 wt %) than any of the other systems in Table 1 or Table 2. Finally, the systems of E1 and E3 were both more selective for 1-octene relative to the system employing the more sterically hindered 1-triptycenyl-PNP ligand (E1: 68.7 wt % C$_8$, E3: 72.1 wt % C$_8$, C3: 63.2 wt % C$_8$).

The invention claimed is:

1. A catalyst system comprising:
   a pre-catalyst comprising one or more chromium compounds coordinated with a ligand; and
   a co-catalyst comprising one or more organoaluminum compounds,
   wherein:
   the ligand has a structure according to formula (I):

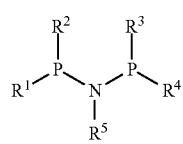

(I)

$R^1$, $R^2$, $R^3$, and $R^4$ are independently chosen from (C$_6$-C$_{60}$) aryl, optionally substituted with one or more $R^S$, wherein $R^S$ is a (C$_1$-C$_{50}$) hydrocarbyl or a (C$_1$-C$_{50}$) heterohydrocarbyl; and $R^5$ is a (C$_9$-C$_{60}$) aryl or a (C$_4$-C$_{60}$) heteroaryl, optionally substituted with one or more $R^S$, wherein $R^S$ is a (C$_1$-C$_{50}$) hydrocarbyl or a (C$_1$-C$_{50}$) heterohydrocarbyl, provided that $R^5$ is not naphthyl or triptycenyl.

2. The catalyst system of claim 1, wherein the one or more chromium compounds comprises one or more of an organic chromium salt, an inorganic chromium salt, a chromium organometallic complex, or combinations of these.

3. The catalyst system of claim 1, wherein the one or more chromium compounds comprises one or more of chromium trichloride tris-tetrahydrofuran complex, (benzene)tricarbonyl chromium, chromium (III) octanoate, chromium (III) acetylacetonoate, chromium hexacarbonyl, chromium (III) 2-ethylhexanoate, or combinations of these.

4. The catalyst system of claim 1, wherein $R^1$, $R^2$, $R^3$ and $R^4$ are independently chosen from phenyl, biphenyl, naphthyl, anthracenyl, or phenoxy.

5. The catalyst system of claim 1, wherein the co-catalyst comprises an aluminoxane or derivative thereof.

6. The catalyst system of claim 1, wherein $R^5$ is a fused polycyclic (C$_8$-C$_{40}$) aryl.

7. The catalyst system of claim 1, wherein $R^5$ is substituted anthracenyl, unsubstituted anthracenyl, substituted pyrenyl, or unsubstituted pyrenyl.

8. A method for tetramerizing ethylene to form 1-octene, the method comprising contacting ethylene with the catalyst system of claim 1 to form a product comprising 1-octene.

9. A method for tetramerizing ethylene to form 1-octene, the method comprising contacting ethylene with the catalyst system of claim 1 in a reactor, at a reactor pressure; and at a reactor temperature.

10. The method for tetramerizing ethylene to form 1-octene according to claim 9, wherein the reactor is a solution polymerization reactor.

11. The method for tetramerizing ethylene to form 1-octene according to claim 10, wherein the solution polymerization reactor further comprises an organic solvent.

12. The method for tetramerizing ethylene to form 1-octene according to claim 9, wherein the reactor pressure is from 2 bar to 100 bar.

13. The method for tetramerizing ethylene to form 1-octene according to claim 9, wherein the reactor temperature is from 30° C. to 180° C.

14. The method for tetramerizing ethylene to form 1-octene according to claim 9, wherein the reactor pressure is from 10 bar to 60 bar; and at a reactor temperature from 30° C. to 100° C., wherein the solution polymerization reactor further comprises chlorobenzene.

* * * * *